(12) United States Patent
Tsujimoto et al.

(10) Patent No.: US 10,076,897 B2
(45) Date of Patent: Sep. 18, 2018

(54) METHOD AND APPARATUS FOR PRODUCING A GRANULAR POWDER-CONTAINING SHEET

(71) Applicant: ZUIKO CORPORATION, Osaka (JP)

(72) Inventors: Yoshiaki Tsujimoto, Osaka (JP); Yukihiko Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 478 days.

(21) Appl. No.: 14/654,318

(22) PCT Filed: Dec. 25, 2013

(86) PCT No.: PCT/JP2013/084711
§ 371 (c)(1),
(2) Date: Jun. 19, 2015

(87) PCT Pub. No.: WO2014/104115
PCT Pub. Date: Jul. 3, 2014

(65) Prior Publication Data
US 2015/0352824 A1 Dec. 10, 2015

(30) Foreign Application Priority Data

Dec. 25, 2012 (JP) .................. 2012-281430
Jun. 25, 2013 (JP) .................. 2013-132844

(51) Int. Cl.
*B32B 37/00* (2006.01)
*B32B 37/20* (2006.01)
(Continued)

(52) U.S. Cl.
CPC ........ *B32B 37/20* (2013.01); *A61F 13/15634* (2013.01); *A61F 13/15658* (2013.01);
(Continued)

(58) Field of Classification Search
CPC . B32B 37/20; B32B 37/0053; B32B 37/0076; B32B 38/06; A61F 13/15634;
(Continued)

(56) References Cited

U.S. PATENT DOCUMENTS 5,762,712 A     6/1998  Sohn
2006/0021695 A1* 2/2006  Blessing ........... A61F 13/15658
                                                156/196
(Continued)

FOREIGN PATENT DOCUMENTS

EP     1621167 A2    2/2006
EP     2609898 A1    7/2013
(Continued)

OTHER PUBLICATIONS

Extended European Search Report for Application No. PCT/JP2013/084711, dated Jul. 26, 2016.
(Continued)

*Primary Examiner* — James Sells
(74) *Attorney, Agent, or Firm* — Marshall, Gerstein & Borun LLP

(57) ABSTRACT

Provided is a method for producing a granular powder-containing sheet containing a granular powder in separated container rooms between two sheet materials. After the container rooms are formed in a first sheet material, the first sheet material is transported on the circumferential surface of an anvil roller. In the process of transportation, the granular powder that is fed from a granular powder feeding hopper through a feeding passage is received in the container rooms. Thereafter, the container rooms are covered with a second sheet material, and the two sheet materials are joined to each other on the peripheries of the container rooms.

12 Claims, 9 Drawing Sheets

(51) Int. Cl.
*B32B 38/06* (2006.01)
*A61F 13/532* (2006.01)
*A61F 13/15* (2006.01)

(52) U.S. Cl.
CPC ...... *A61F 13/5323* (2013.01); *B32B 37/0053* (2013.01); *B32B 37/0076* (2013.01); *B32B 38/06* (2013.01); *B32B 2310/028* (2013.01); *B32B 2555/02* (2013.01); *Y10T 156/1039* (2015.01)

(58) Field of Classification Search
CPC . A61F 13/15658; A61F 13/5323; B29C 65/08
USPC ........................................................ 156/73.1
See application file for complete search history.

(56) References Cited

U.S. PATENT DOCUMENTS

| | | |
|---|---|---|
| 2006/0024433 A1 | 2/2006 | Blessing et al. |
| 2006/0048880 A1 | 3/2006 | Blessing et al. |
| 2008/0215166 A1 | 9/2008 | Blessing et al. |
| 2010/0051166 A1 | 3/2010 | Hundorf et al. |
| 2010/0224311 A1 | 9/2010 | Blessing et al. |
| 2011/0017398 A1 | 1/2011 | Blessing et al. |
| 2012/0203527 A1 | 8/2012 | Blessing et al. |
| 2013/0025792 A1 | 1/2013 | Ninomiya et al. |
| 2013/0112348 A1 | 5/2013 | Blessing et al. |
| 2013/0124170 A1 | 5/2013 | Blessing et al. |
| 2013/0284361 A1 | 10/2013 | Tsujimoto et al. |
| 2014/0220241 A1 | 8/2014 | Blessing et al. |
| 2014/0318694 A1 | 10/2014 | Blessing et al. |
| 2015/0065986 A1 | 3/2015 | Blessing et al. |

FOREIGN PATENT DOCUMENTS

| | | |
|---|---|---|
| JP | 2007130818 A | 5/2007 |
| JP | 2008508052 A | 3/2008 |
| JP | 2011177299 A | 9/2011 |
| WO | WO-2012108331 A1 | 8/2012 |

OTHER PUBLICATIONS

International Search Report and Written Opinion for Application No. PCT/JP2013/084711, dated Mar. 25, 2014.

* cited by examiner (a)

(b)

(c)

(f)

(e)

(d)

METHOD AND APPARATUS FOR PRODUCING A GRANULAR POWDER-CONTAINING SHEET

TECHNICAL FIELD

The present invention relates to producing a granular powder-containing sheet, and more specifically, to a method and an apparatus for producing a granular powder-containing sheet that allow easy handling of a granular powder in the production of the granular powder-containing sheet containing the granular powder between two sheet materials.

BACKGROUND ART

Disposable wearable goods such as disposable diapers and the like are typically provided with an absorber for absorbing liquids such as urine and the like. Among the absorbers are those provided with a granular powder of a highly absorptive resin (Super Absorbent Polymer, hereinafter occasionally referred to as SAP) to absorb liquids efficiently.

Conventionally, as to a method for producing a granular powder-containing sheet containing the granular powder between two sheet materials, there has been a proposal on a method and an apparatus for producing a granular powder-containing sheet, in which, for example, separated container rooms are formed between the two sheet materials and the granular powder of SAP or the like is received in the container rooms (see, for example, Patent Literature 1).

The conventional manufacturing apparatus is provided with a roller-shaped transfer device and a roller-shaped carrier supporting means, of which the circumferential surfaces each have a plurality of recessed portions formed in a predetermined pattern. In one of the sheet materials that is fed onto the circumferential surface of the carrier supporting means, hollows are formed at the recessed portions by a reduced pressure, and the hollows serve as the container rooms. Meanwhile, a predetermined amount of a granular powder fed from a granular powder feeding hopper and received in each of the recessed portions on the circumferential surface of the transfer device is transferred, at a receiving position, into each of the hollows in the sheet material. Thereafter, a second sheet material is disposed over the sheet material, and subsequently, the two sheet materials are joined to each other on the peripheries of the hollows.

CITATION LIST

Patent Literature

PTL 1: Japanese Unexamined Patent Application Publication No. 2008-508052

SUMMARY OF INVENTION

Technical Problem

In the prior art, the hollows are formed in one of the sheet materials by a reduced pressure in the recessed portions on the circumferential surface of the carrier supporting means; however, since the sheet material is made of a material having a good liquid or gas permeability, for example, nonwoven fabric or the like, the shape of the hollows is likely to vary depending on the degree of vacuum, the feeding rate of the sheet material, and the like. In particular, the higher the production rate is, the harder it becomes to form the hollows in a predetermined shape. Further, in the conventional production apparatus, since the granular powder is first received in the recessed portions on the circumferential surface of the transfer device and then transferred into the hollows in the first sheet material, problems are that complicated devices are needed for handling the granular powder and that the granular powder is not easy to handle, for example, is likely to spill out of each of the devices.

The present invention is directed to solving the technical problems, and therethrough to providing a method and an apparatus for producing a granular powder-containing sheet that allow easy handling of a granular powder in the production of the granular powder-containing sheet containing the granular powder in container rooms formed between two sheet materials.

Solution to Problem

In order to solve the problems, the present invention, when explained, for example, based on FIG. 1 to FIG. 9 that show embodiments of the present invention, is constituted as follows.

That is, Aspect 1 of the present invention relates to a method for producing a granular powder-containing sheet, and is a method for producing a granular powder-containing sheet containing a granular powder (6) in separated container rooms (14) formed between two sheet materials (4, 8), the method comprising: forming the container rooms (14) in a first sheet material (4); thereafter transporting the first sheet material (4) on a circumferential surface of an anvil roller (2); during the transporting process, allowing the granular powder (6) fed from a granular powder feeding hopper (11) through a feeding passage (12) to be received in the container rooms (14); thereafter covering the container rooms (14) with a second sheet material (8); and joining the two sheet materials (4, 8) to each other on the peripheries of the container rooms (14).

Aspect 2 of the present invention is an apparatus for producing a granular powder-containing sheet containing a granular powder (6) in separated container rooms (14) formed between a first sheet material (4) and a second sheet material (8), the apparatus comprising: an anvil roller (2) for transporting a first sheet material (4) on the circumferential surface thereof; a granular powder feeding hopper (11) for feeding the granular powder (6) continuously; a feeding passage (12) for guiding the granular powder (6) downward from the granular powder feeding hopper (11); a joining means (10) for joining the two sheet materials (4, 8) to each other; a first feeding means (5) for feeding the first sheet material (4); and a second feeding means (9) for feeding the second sheet material (8), wherein a receiving position (17, 17a) and a joining position (18) are located along the circumferential surface of the anvil roller (2) in this order from upstream of the rotational direction thereof; the first feeding means (5) is provided so as to be capable of feeding the first sheet material (4) to an upstream side of the receiving position (17, 17a); a lower end of the feeding passage (12) faces, at the receiving position (17, 17a), the container rooms (14) formed in the first sheet material (4); the second feeding means (9) is capable of feeding the second sheet material (8) to either the joining position (18) or in between the joining position (18) and the receiving position (17, 17a); and the joining means (10) faces the anvil roller (2) at the joining position (18).

Since the granular powder is fed from the granular powder feeding hopper through the feeding passage and is allowed to be received in the container rooms, the granular powder is prevented from spilling out of the apparatus, and thus can be handled easily.

The method for forming the container rooms in the first sheet material is not particularly limited. However, preferably, a shaping roller having a plurality of protruding portions on its circumferential surface is disposed so as to face the anvil roller so that a plurality of recessed portions provided on the circumferential surface of the anvil roller mesh with the protruding portions; the first sheet material is fed onto the circumferential surface of the shaping roller; and thereby container rooms are formed in the first sheet material, because, in this case, the container rooms with a predetermined shape can be surely formed even when the production is performed at a high speed.

The recessed portions that mesh with the protruding portions of the shaping roller in the formation of the above-mentioned container rooms may be provided on the circumferential surface of a second shaping roller that is disposed so as to face said shaping roller. However, since the above-mentioned anvil roller has recessed portions that mesh with the protruding portions, the container rooms may preferably be formed by the recessed portions of the anvil roller and the protruding portions that mesh with each other. In this case, the second shaping roller is not required and the apparatus is simplified.

Means for joining the two sheet materials to each other is not particularly limited, and any joining means such as welding using a heated roller, pressure gluing using an adhesive applied to either one of the sheet materials and using a pressurizing roller, etc. can be employed. However, it is preferable to join the two sheet materials to each other by welding using an ultrasonic welding device, because thereby overheating of the granular powder and other parts of the two sheet materials can be prevented, and the joining strength can easily be set to a predetermined value.

The first sheet material provided, at the shaping position, with the container rooms in a predetermined shape is transported along the circumferential surface of the anvil roller. At this stage, it is preferable to reduce the pressure inside the recessed portions of the anvil roller so that the first sheet material is transported to the joining position with the container rooms thereof sucked and held in the recessed portions so as not to move or slip off the recessed portions. Means for reducing the pressure inside the recessed portions is not limited to a specific configuration; however, typically, an evacuation device that is communicably connected to interiors of the recessed portions via a suction passage is provided.

The shape and the structure of the feeding passage are not particularly limited as long as continuous feeding of the granular powder from the granular powder feeding hopper can be achieved. However, since the granular powder-containing sheet is, after having been produced continuously, cut into unit lengths suitable for use in disposable wearable goods or the like and separated, if any container room containing the granular powder exists at portions where the cutting is made, there arise problems of spill and fall of the granular powder at the time of cutting and of rapid wear of and damage to the cutting blade due to the hardness of the granular powder. Therefore, the feeding passage is preferably provided with an excluding means to exclude part of the granular powder flowing in the feeding passage to the outside of the feeding passage so that the granular powder can be intermittently fed from the granular powder feeding hopper to the container rooms, that is, the feeding of the granular powder to the container rooms can be stopped at portions to be cut, not only preventing the spill and fall of the granular powder at the time of cutting but also reducing the wear of and damage to the cutting blade.

The receiving position can be provided at any part as long as the granular powder can be fed to the container rooms. After arriving at the anvil roller, the granular powder fed from the feeding passage moves downward along the circumferential surface of the anvil roller due to gravity, regardless of the granular powder receiving position on the anvil roller. In this stage, if the receiving position is located upstream of the top of the anvil roller with respect to the rotational direction thereof, since the direction of the movement of the granular powder on the anvil roller (toward the upstream side with respect to the rotational direction) is opposite to the rotational direction of the anvil roller, the granular powder is not smoothly received in the container rooms, and is likely to spill toward the upstream side with respect to the rotational direction.

Accordingly, the receiving position of the granular powder is preferably provided on the downstream side of the top of the anvil roller with respect to the rotational direction, because, in this case, the direction of the movement of the granular powder on the anvil roller (toward the downstream side in the rotational direction) is the same as the rotational direction of the anvil roller. Thus, the granular powder is smoothly received in the container rooms.

The excluding means can be configured in a variety of ways as long as it has a structure that can exclude part of the granular powder flowing in the feeding passage to the outside of the feeding passage. For example, part of the granular powder may be excluded to the outside of the feeding passage by a high pressure air stream from a high pressure air jet generator disposed as the excluding means. However, preferred is a configuration in which the feeding passage comprises an open-close means for opening and closing the feeding passage and thereby part of the granular powder can be excluded to the outside of the feeding passage, because, in this case, part of the granular powder, that is, the granular powder existing within a predetermined range in a feeding direction, can surely be excluded to the outside of the feeding passage.

The configuration of the open-close means is not particularly limited as long as it can open and close the feeding passage, for example, by a passage switching member that is disposed in the feeding passage and is capable of switching to a collecting passage. However, the open-close means more preferably comprises an open-close member that opens and closes the feeding passage by intersecting the feeding passage. With this open-close member, the feeding passage can be opened and closed surely and quickly, and thus, part of the granular powder, that is, the granular powder existing within a predetermined range in a feeding direction can surely be excluded to the outside of the feeding passage, achieving a so-called high-speed and sharp intermittent feeding, in which the boundary between a portion of the granular powder to be fed and a portion of the granular powder to be excluded is clear. The shape of the open-close member is not particularly limited; however, a thinner member, such as a plate-like one, is more preferred, because such a thin member is less likely to disturb the flow of the granular powder when intersecting the feeding passage; accordingly, a near I-shaped one, a near L-shaped one, or the like (in plan view) having a structure that ensures secure closing of the feeding passage can be employed. Preferred is an open-close member that meets the specifications of the apparatus for producing the granular powder-containing sheet and requires only a small retraction space.

The open-close member has only to be capable of opening and closing the feeding passage by intersecting the feeding passage, but preferably is configured to move almost parallel to a tangential line of the circumferential surface of the anvil roller at the receiving position, because, in this case, the open-close member can be disposed close to the receiving position, and thereby disturbance to the flow of the granular powder on the downstream side of the open-close position can be suppressed.

The second sheet material is preferably fed at a position that is on the downstream side of the granular powder receiving position with respect to the rotational direction of the anvil roller and is as close as possible to the receiving position so that the container rooms having received the granular powder are immediately covered with the second sheet material, because thereby the granular powder is prevented from being scattered around the apparatus. Specifically, regarding the position at which the second sheet material is fed, for example, the length obtained by subtracting the thickness of the second sheet material from the distance between the receiving position and the feeding position is preferably about 5 mm or less, and more preferably 2 mm or less.

The structure of the guide member for guiding the second sheet material to the joining position or in between the joining position and the receiving position is not particularly limited, and a small diameter guide roller and/or a guide bar can be used; however, a guide panel made of metallic plate, ceramics plate, or the like is preferably provided as the guide member, because, in this case, an end of the guide panel can be brought as close as possible to the receiving position, and there is no risk of failure attributable to rotational parts, guiding the second sheet material surely with a simple mechanism. Furthermore, since the guide panel is disposed between the second sheet material guided to the feeding position and the anvil roller, the second sheet material can be advantageously prevented from being affected by the reduced pressure on the surface of the anvil roller.

Advantageous Effects of Invention

According to the present invention, since a granular powder is fed from a granular powder feeding hopper through a feeding passage and allowed to be received in container rooms, the granular powder can be effectively prevented from spilling out of the apparatus in the feeding process and can be handled easily in the production process.

DESCRIPTION OF EMBODIMENTS

The present invention will be concretely described below based on the drawings. It goes without saying that the present invention is not limited to the embodiments described below, and can be modified or changed in many ways within the technical scope of the present invention.

Embodiment 1

Figure 1:
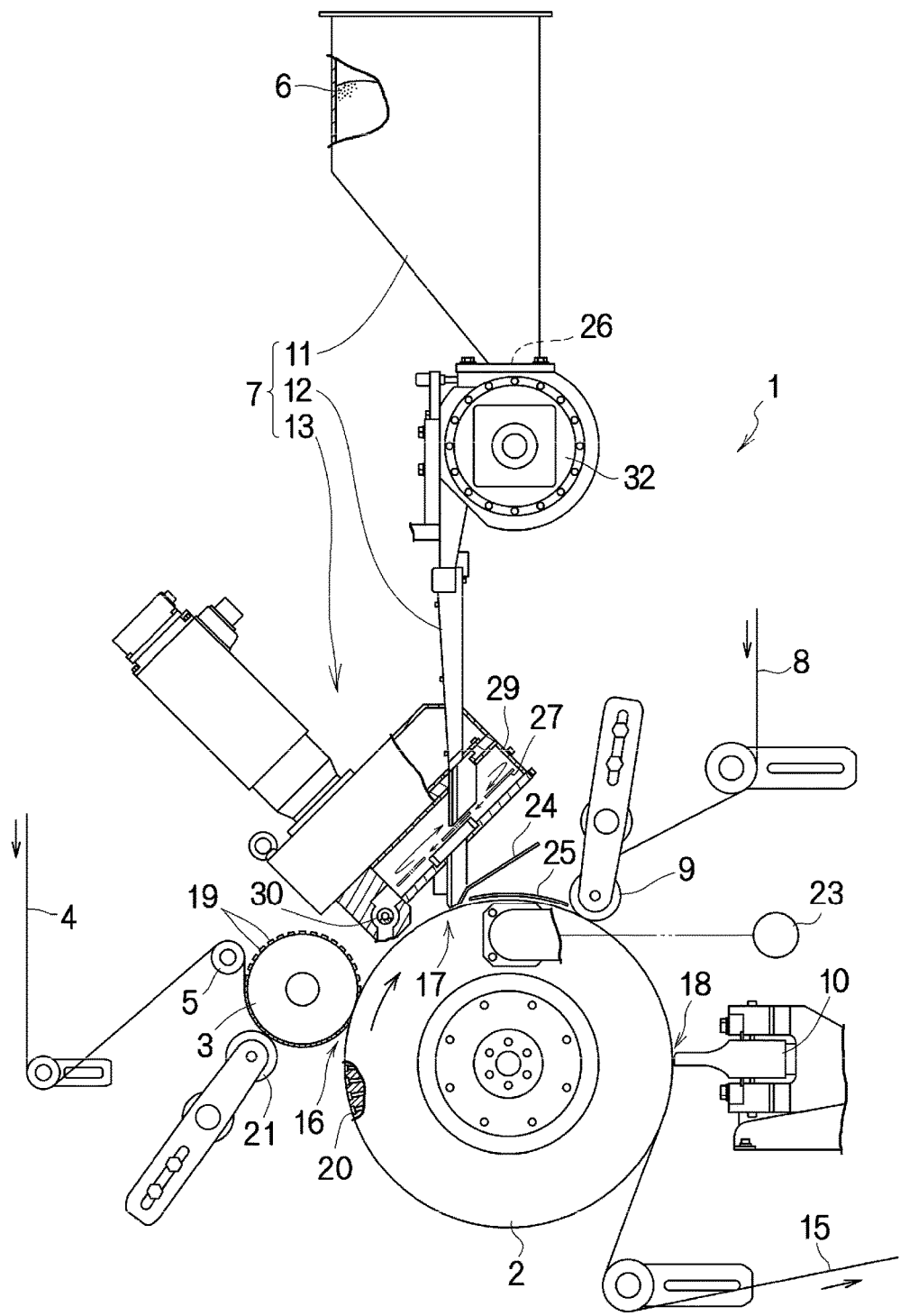
FIG. 1 is a schematic view of an apparatus for producing a granular powder-containing sheet according to Embodiment 1 of the present invention.

As shown in FIG. 1, an apparatus (1) for producing a granular powder-containing sheet comprises: an anvil roller (2); a shaping roller (3) that faces the anvil roller (2); a first feeding means (5) that feeds a first sheet material (4) to the circumferential surface of the shaping roller (3); a granular powder feeding device (7) that feeds a granular powder (6) which is a highly absorptive resin (SAP); a second feeding means (9) that feeds a second sheet material (8) to a circumferential surface of the anvil roller (2); and a joining means (10) that faces the anvil roller (2) and joins the two sheet materials (4, 8) to each other.

Further, the granular powder feeding device (7) comprises: a granular powder feeding hopper (11) that stores the granular powder (6); a feeding passage (12) that guides the granular powder (6) from the granular powder feeding hopper (11) to an upper part of the anvil roller (2); and an open-close means (13) as an excluding means provided in a middle part of the feeding passage (12) in the vertical direction. Here, in this embodiment, the open-close means (13) is provided in the middle part of the feeding passage (12) in the vertical direction, but the position of the open-close means (13) is not limited thereto; for example, in other embodiments, the open-close means (13) has only to be provided in the feeding passage (12), and may be provided at an upper end portion or a lower end portion of the feeding passage (12).

Figure 2:
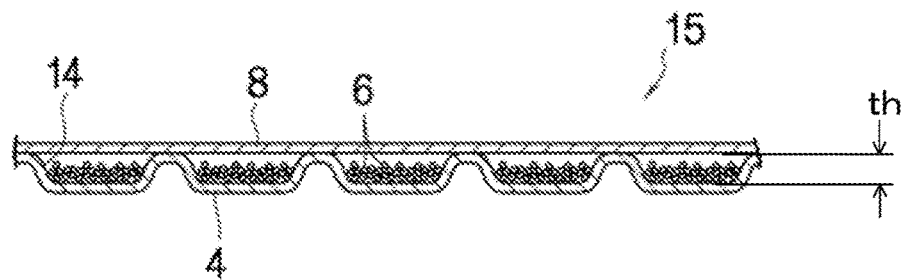
FIG. 2 is a cross-sectional view of a main part of the granular powder-containing sheet produced by the apparatus according to Embodiment 1 or Embodiment 2 of the present invention.

Then, using the production apparatus (1), is produced a granular powder-containing sheet (15), as shown in FIG. 2, containing a granular powder (6) in separated container rooms (14) between the first sheet material (4) and the second sheet material (8). Here, in this embodiment, explanation is made on a case where the granular powder is SAP, but the granular powder is not limited thereto; for example, in other embodiments, the granular powder may be one other than SAP, and may be grains, a finer powder, or a fibrous material.

Figure 3:
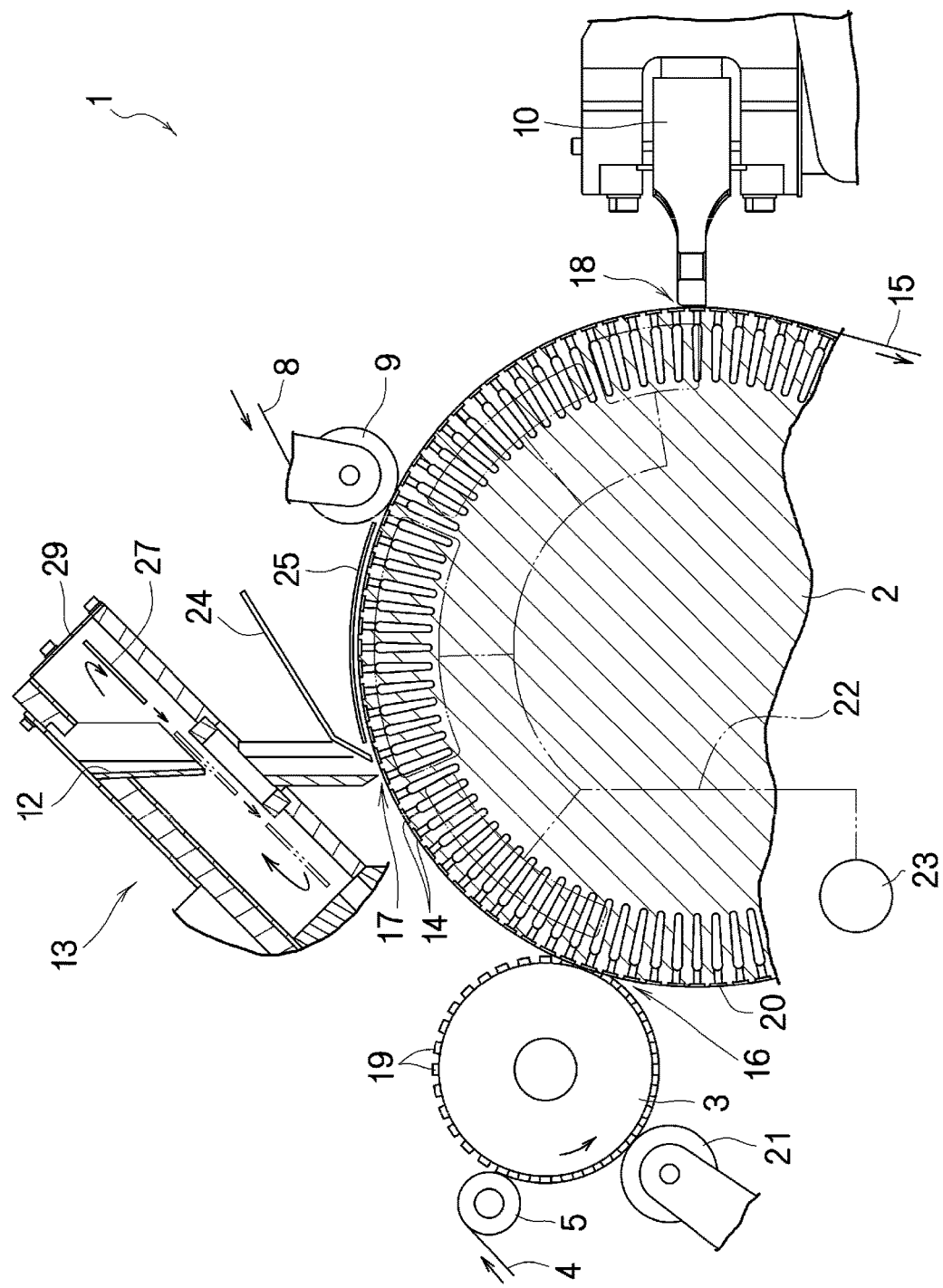
FIG. 3 is an enlarged cross-sectional view of a main part of the production apparatus according to Embodiment 1 of the present invention.

As shown in FIG. 3, a shaping position (16) is provided on the circumferential surface of the shaping roller (3), and a receiving position (17) and a joining position (18) are provided along the circumferential surface of the anvil roller (2) in this order from upstream of the rotational direction thereof.

Onto the circumferential surface of the shaping roller (3), the first sheet material (4) is fed to an upstream side of the shaping position (16) by the first feeding means (5). The shaping roller (3) faces the anvil roller (2) at the shaping position (16), and the first sheet material (4) is passed between the two rollers. The shaping roller (3) is provided with a plurality of protruding portions (19) on its circumferential surface, whereas the anvil roller (2) is provided with recessed portions (20) on its circumferential surface, and the recessed portions (20) mesh with the protruding portions (19) of the shaping roller (3). Also, a nip roller (21) is disposed so as to face the shaping roller (3).

The lower end opening of the feeding passage (12) of the granular powder feeding device (7) faces the anvil roller (2) and faces, at the receiving position (17), the container rooms (14) formed on the upper surface of the first sheet material (4) passing through the receiving position (17). In this regard, the lower end of the feeding passage (12) is preferably disposed close to the surface of the anvil roller (2). Although the distance between the lower end of the feeding passage (12) and the surface of the anvil roller (2) is determined depending on the amount of the granular powder (6) to be fed, the distance is preferably at least equal to the thickness of the granular powder to be fed, that is, for example, the depth (th) of the container rooms (14) shown in FIG. 2. On the other hand, if the distance between the lower end of the feeding passage (12) and the surface of the anvil roller (2) is excessively larger than the depth (th), the granular powder (6) fed from the feeding passage (12) is unfavorably likely to scatter about due to, for example, an air current resulting from the reduced pressure inside the recessed portions (20) on the surface of the anvil roller (2), as will be described later. To prevent such a disadvantage, the distance between the lower end of the feeding passage (12) and the surface of the anvil roller (2) is preferably 10 mm or less, and more preferably 5 mm or less.

The joining means (10) is formed of an ultrasonic welding device, and the end of its horn is disposed so as to face the anvil roller (2) at the joining position (18).

The second feeding means (9) is disposed so as to feed the second sheet material (8) in between the receiving position (17) and the joining position (18).

Inside the anvil roller (2) is formed a suction passage (22), and through the suction passage (22), interiors of the recessed portions (20) are communicably connected to an evacuation device (23). By the evacuation device (23), interiors of the recessed portions (20) at least within the range from the shaping position (16) to the joining position (18) are vacuumed.

Of the feeding passage (12), the part lower than the open-close means (13) has a side surface open to the external space so that the granular powder (6) passing through the feeding passage (12) will not be adversely affected by the reduced pressure inside the recessed portions (20). Also, a baffle plate (24) is disposed between the open side surface of the lower part of the feeding passage (12) and the anvil roller (2). The baffle plate (24) prevents the air current caused by the reduced pressure and/or the like from unfavorably influencing the feeding of the granular powder (6).

Further, a vacuum retention member (25), such as one made of a perforated metallic sheet, is provided along the circumferential surface of the anvil roller (2) so as to face an area from the receiving position (17) to the feeding position of the second sheet material (8), and thereby the vacuumed state inside the recessed portions (20) passing through the area is appropriately maintained.

Figure 4:
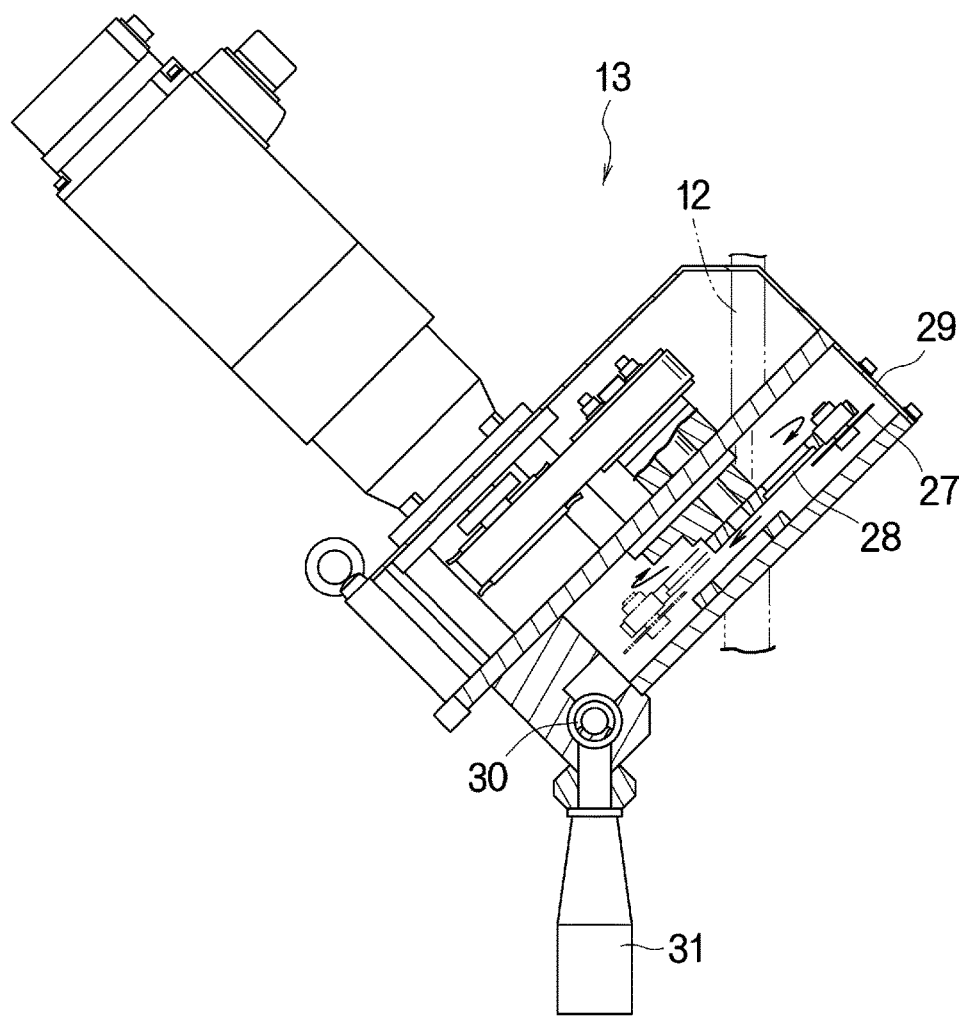
FIG. 4 is a cross-sectional view of an open-close device used in a granular powder feeding device according to Embodiment 1 of the present invention.
Figure 5:
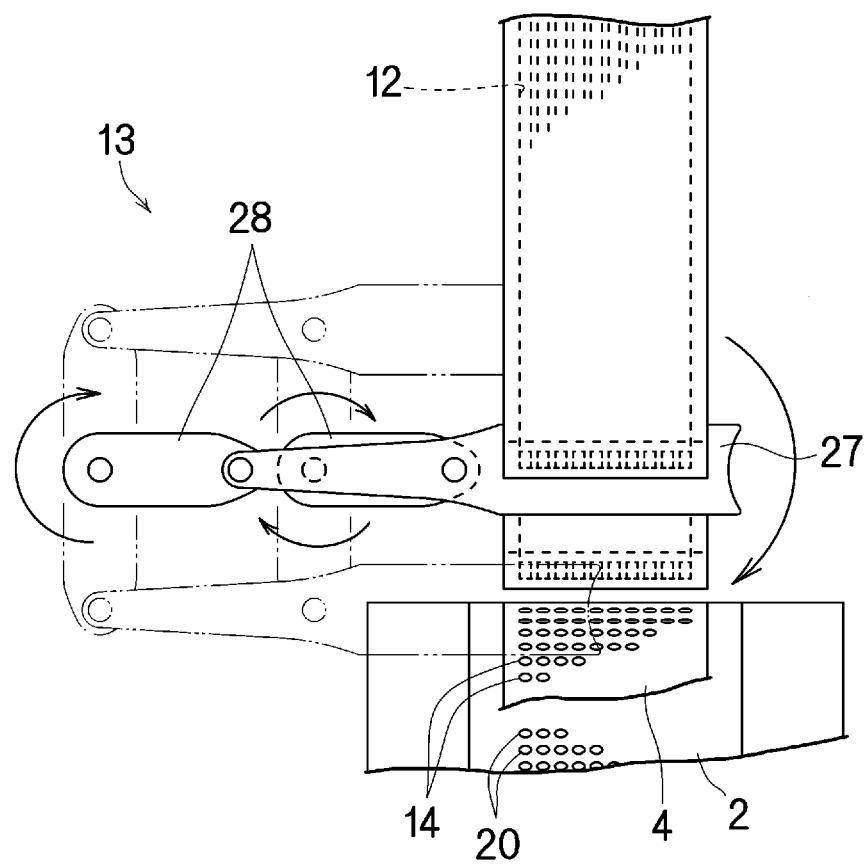
FIG. 5 is an explanatory drawing for a movement of an open-close member according to Embodiment 1 of the present invention.

The granular powder feeding device (7) comprises an amount regulating device (32) attached to an outlet (26) of the granular powder feeding hopper (11), and a predetermined amount of the granular powder (6) is sent out downward from the outlet (26). The feeding passage (12) is disposed so as to extend downward from the outlet (26). The granular powder (6), being sent out from the amount regulating device (32) downward along the feeding passage (12), flows smoothly in the feeding passage (12). The open-close means (13) disposed in the middle part of the feeding passage (12) in the vertical direction is provided with, as shown in FIG. 4 and FIG. 5, a plate-like open-close member (27) that is I-shaped in plan view. The open-close member (27), which intersects the feeding passage (12), is capable of opening and closing the feeding passage (12) and thereby excluding part of the granular powder flowing in the feeding passage (12) to the outside of the feeding passage (12).

As shown in FIG. 5, the transverse cross-sectional shape of the feeding passage (12) is long in the width direction of the first sheet material (4). Also, the open-close member (27) is longer in the width direction of the first sheet material (4) than the width of the feeding passage (12) so as to be capable of closing the feeding passage (12), and is driven in a direction orthogonal to the width direction of the first sheet material (4) so as to intersect the feeding passage (12). Specifically, two positions of the open-close member (27) are rotationally driven via link arms (28) respectively, and with a quadruple link thus formed, the open-close member (27) is kept parallel and is unidirectionally rotated.

The feeding passage (12) having a transverse cross-sectional shape long in the width direction of the first sheet material (4) has only to be long in the width direction as a whole feeding passage (12), and may be divided into a plurality of separate passages of which respective widths are short. In this case, since the granular powder (6) divided into the respective separate passages is fed as it is from the lower end opening into the container rooms (14), the granular powder (6) is uniformly fed over the entire width of the first sheet material (4). In particular, inlets at the upper ends of the respective separate passages are preferably provided with incoming amount changing means, such as guide plates or the like, so that the granular powder (6) sent out from the amount regulating device (32) is divided equally at the inlets of the respective separate passages, because, in this case, the granular powder (6) can be fed more uniformly over the entire width of the first sheet material (4).

Also, the open-close member (27), as shown in FIG. 4, is driven so as to diagonally intersect the feeding passage (12) from an upper part of one side of the feeding passage (12) to a lower part of the other side.

As shown in FIG. 4, the open-close means (13) is provided with a casing (29) that encloses part of the feeding passage (12) at which it is opened and closed, and the open-close member (27) is rotationally driven inside the casing (29). Inside the casing (29), at a lower part thereof, a mechanical discharge means (30), such as a screw transportation device, is provided, and a discharge passage (31) is formed at the lower part of the casing (29). Preferably, the volume of the inner space of the casing (29) is large enough in order to suppress the influence of the air current occurring inside the casing (29) due to the reduced pressure inside the recessed portions (20) on the surface of the anvil roller (2), on the flow of the granular powder. Even if such an air current occurs, when the volume of the inner space of the casing (29) is large enough, the velocity of the air current will not become high, so that its influence on the flow of the granular powder can be suppressed.

Next, a method for producing a granular powder-containing sheet using the production apparatus will be described.

A first sheet material (4) that is fed onto the circumferential surface of the shaping roller (3) by the first feeding means (5) is passed, at the shaping position (16), between the shaping roller and the anvil roller (2), and thereby container rooms (14) are formed in the first sheet material (4). Since the container rooms (14) are shaped by the protruding portions (19) and the recessed portions (20) that mesh with each other, the container rooms (14) with a predetermined shape can be surely formed even when the production is performed at a high speed. The ease of shaping of the first sheet material (4) depends on the thickness, the material, etc. thereof; however, since its shaping is generally easier in a heated state, a heating means is preferably provided in the shaping roller (3) or its proximity. The heating means may be, for example, a heating device provided inside the shaping roller (3), a hot-air blower that blows heated air to the first sheet material (4), or the like. The first sheet material (4) is transported, on the circumferential surface of the anvil roller (2), downstream in the rotational direction thereof with the container rooms (14) sucked and held in the recessed portions (20) due to the reduced pressure inside the recessed portions (20).

In the process of the transportation, when the container rooms (14) reach the receiving position (17), the granular powder (6) fed from the granular powder feeding hopper (11) through the feeding passage (12) is allowed to be received in the container rooms (14). At this time, since the transverse cross-sectional shape of the feeding passage (12) is long in the width direction of the first sheet material (4), the granular powder (6) is simultaneously fed to and received in each of the container rooms (14) arranged in a row in the width direction of the first sheet material (4). In this case, as described above, when the distance between the lower end of the feeding passage (12) and the surface of the anvil roller (2) is equal to or more than the thickness of the granular powder to be fed, that is, equal to or more than the depth (th) of the container rooms (14) shown in FIG. 2 and 10 mm or less, the granular powder (6) fed from the feeding passage (12) can be prevented from scattering about due to, for example, an air current resulting from the reduced pressure inside the recessed portions (20) on the surface of the anvil roller (2).

Thus, when the lower end of the feeding passage (12) is close to the surface of the anvil roller (2) and the distance to the container rooms (14) is short, the granular powder falling from the feeding passage (12) is allowed to be efficiently received in intended container rooms. That is, as the result of the short distance between the lower end of the feeding passage (12) and the surface of the anvil roller (2), the granular powder (6) intermittently fed via the open-close member (27) is allowed to be efficiently received in intended container rooms (14) without scattering about when the feeding passage (12) is opened, and is stopped from flowing into corresponding container rooms (14) when the feeding passage (12) is closed. Consequently, the state with the feeding passage (12) closed by the open-close member (27) and the state with the feeding passage (12) open after the open-close member (27) has completely finished traversing the feeding passage (12) are clearly separated, achieving a so-called sharp intermittent feeding of the granular powder.

The first sheet material (4) is further transported, and when the container rooms (14) reach the feeding position of the second sheet material (8), the container rooms (14) are covered with the second sheet material (8). The two sheet materials (4, 8) in a superposed state are further transported, and when the container rooms (14) reach the joining position (18), the two sheet materials (4, 8) are joined to each other on the peripheries of the container rooms (14) by ultrasonic welding as the joining means (10) described above.

In the feeding of the granular powder (6) to the container rooms (14), with use of the open-close member (27) of the open-close means (13) for opening and closing the feeding passage (12), part of the granular powder flowing in the feeding passage (12) is excluded to the outside of the feeding passage (12); thereby the granular powder (6) is intermittently fed from the granular powder feeding hopper (11) into the container rooms (14).

That is, when the rotationally driven open-close member (27) intersects the middle part of the feeding passage (12) in the vertical direction, the feeding passage (12) is closed. The granular powder (6) blocked during this period by the open-close member (27) in the feeding passage (12) is excluded to the outside of the feeding passage (12), and the feeding of the granular powder (6) is halted. Then, when the open-close member (27) has completely finished traversing the feeding passage (12) and gets out of the feeding passage (12), the blockage is released, and hence the feeding of the granular powder (6) into the container rooms (14) is resumed. Thus the granular powder (6) is intermittently fed downward into the container rooms (14).

Since the open-close member (27) is longer in the width direction of the first sheet material (4) than the width of the feeding passage (12) and intersects the feeding passage (12) in a direction orthogonal to the width direction of the first sheet material (4), the opening and closing of the feeding passage (12) is achieved at the same time over the entire width thereof. Therefore, the feeding of the granular powder (6) to the respective container rooms (14) arranged in a row in the width direction of the first sheet material (14) is simultaneously started and simultaneously halted.

As the result, the granular powder-containing sheet (15) produced using the production apparatus has parts formed at predetermined intervals where none of the container rooms in a row in the width direction contain the granular powder (6). Accordingly, when the granular powder-containing sheet (15) continuously produced is cut into unit lengths suitable for use in disposable wearable goods or the like, cutting the granular powder-containing sheet (15) at the parts not containing the granular powder (6) can prevent the spill and fall of the granular powder at the time of cutting, and can also prevent rapid wear of and/or damage to the cutting blade.

The open-close member (27) may be moved back and forth between one side and the other side of the feeding passage (12), or moved so as to diagonally intersect the feeding passage (12) from a lower part of one side to an upper part of the other side; however, preferably, as shown in FIG. 4, the open-close member (27) is driven so as to diagonally intersect the feeding passage (12) from an upper part of one side of the feeding passage (12) to a lower part of the other side. As the result, the granular powder (6) spilling and falling from the feeding passage (12) during the intersection is surely excluded to the outside of the feeding passage (12). Since the part of the feeding passage (12) opened and closed by the open-close member (27) is enclosed by the casing (29), the granular powder (6) spilling from the feeding passage (12) due to the open and close operation is caught inside the casing (29) without spilling to the outside. The granular powder (6) caught inside the casing (6) is collected to the lower part of the casing (29), and is discharged from the discharge passage (31) to the outside of the casing (29) by the mechanical discharge means (30).

Embodiment 2

To components common between the drawings used in Embodiment 2 and FIG. 1 to FIG. 5, the same reference numbers are assigned, and explanations for the common components will be omitted here.

Figure 6:
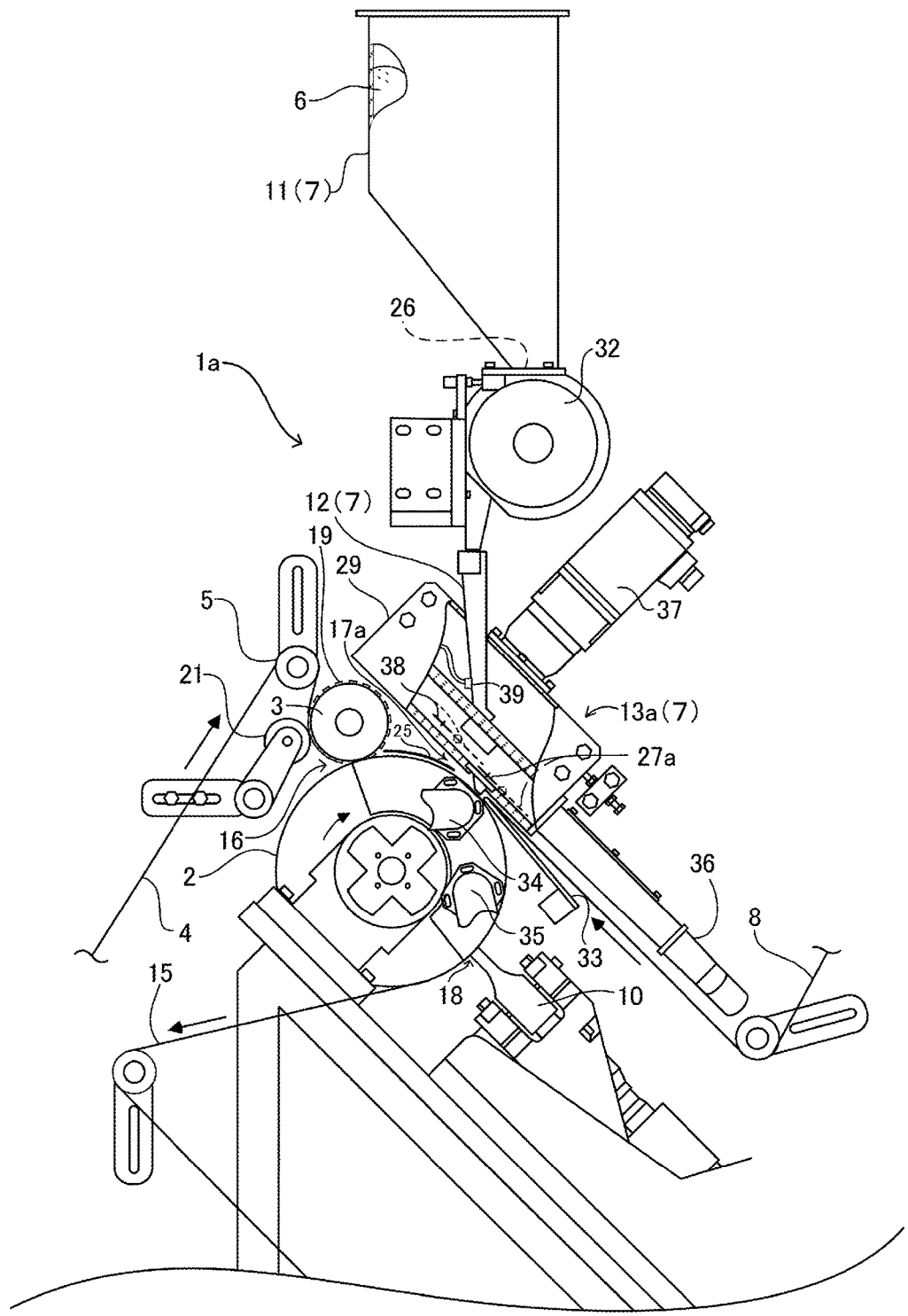
FIG. 6 is a schematic view of an apparatus for producing a granular powder-containing sheet according to Embodiment 2 of the present invention.

FIG. 6 is a schematic drawing of an apparatus for producing a granular powder-containing sheet according to Embodiment 2 of the present invention.

In Embodiment 2, as in Embodiment 1, an apparatus (1a) for producing a granular powder-containing sheet comprises: an anvil roller (2); a shaping roller (3); a first feeding means (5) that feeds a first sheet material (4); a granular powder feeding device (7) that feeds a granular powder (6) which is a highly absorptive resin (SAP); a second feeding means (9) that feeds a second sheet material (8); and a joining means (10) that joins the two sheet materials (4, 8) to each other.

Receiving Position

As in Embodiment 1, a receiving position (17a) and a joining position (18) are provided along the circumferential surface of the anvil roller (2) in this order from upstream of the rotational direction thereof; however, Embodiment 2 is different from Embodiment 1 in that the receiving position (17a) is located downstream of the top of the anvil roller (2) with respect to the rotational direction.

As shown in FIG. 1 and FIG. 3, in Embodiment 1, the receiving position (17) is located upstream of the top of the anvil roller (2) with respect to the rotational direction. Therefore, as will be described below, there is a risk that the granular powder (6) fed from the feeding passage (12) is not received in intended container rooms (14) but spill toward the upstream side with respect to the rotational direction.

After reaching the anvil roller (2), the granular powder (6) fed from the feeding passage (12) moves downward along the circumferential surface of the anvil roller (2) due to gravity, regardless of the receiving position (17 or 17a) on the anvil roller (2).

At this time, if the receiving position (17) is located upstream of the top of the anvil roller (2) with respect to the rotational direction, as shown in FIG. 1 and FIG. 3, since the direction of the movement of the granular powder (6) on the anvil roller (2) is opposite to the rotational direction of the anvil roller (2), the granular powder (6) is not smoothly received in intended container rooms (14), and is likely to spill into different container rooms (14) on the upstream side of the rotational direction.

Figure 7:
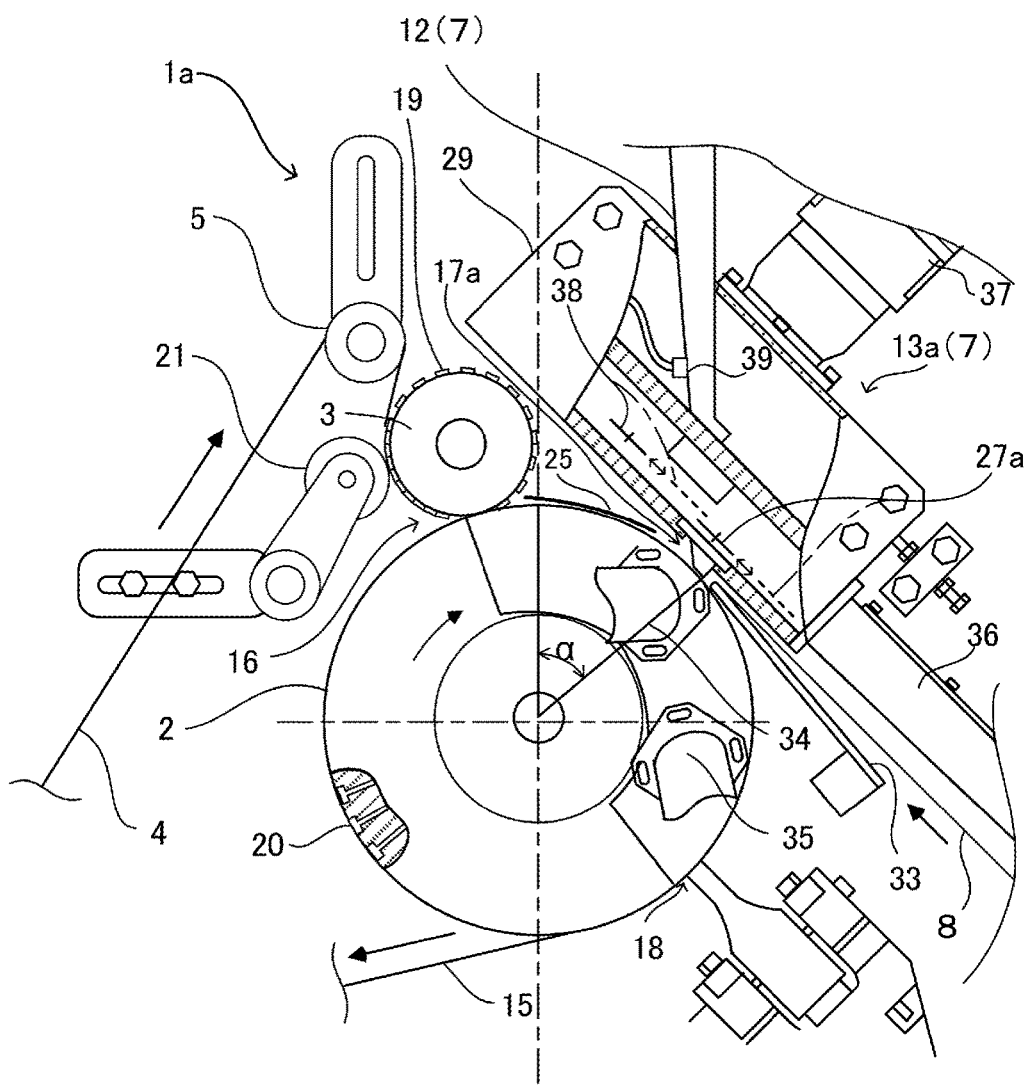
FIG. 7 is an enlarged cross-sectional view of a main part of the production apparatus according to Embodiment 2 of the present invention.

In Embodiment 2, as shown in FIG. 6 and FIG. 7, the receiving position (17a) is located downstream of the top of the anvil roller (2) with respect to the rotational direction. Since the direction of movement of the granular powder (6) on the anvil roller (2) is the same as the rotational direction of the anvil roller (2), the granular powder (6) is smoothly received in intended container rooms (14).

The receiving position (17a) in FIG. 6 and FIG. 7 is, as shown in FIG. 7, located within a range of angle ($\alpha°$) of 30° to 60°, preferably 40° to 50°, toward the downstream side in the rotational direction with respect to a perpendicular line connecting the center of the anvil roller (2) to the top thereof.

Means for Discharging Granular Powder in the Casing

When discharged outside the casing by a mechanical discharge means, there is a risk that the granular powder is damaged by the discharge means. To avoid this, in Embodiment 2, the granular powder is discharged outside the casing by a discharge means using gravity, and where necessary, a suction by an air stream such as suction passage or the like in combination. This configuration can reduce the damage to the granular powder and allow reuse of the granular powder of good quality, and is therefore preferable.

Regarding the occurrence of the air current inside the casing caused by the suction, as the countermeasures thereagainst, the volume of the inner space of the casing is increased as much as possible to suppress the air current inside the casing and an air intake port is provided on the casing, as described above. As the result, the velocity of the air current will not become high and its influence on the flow of the granular powder can be suppressed. For example, as shown in FIG. 6, an air intake port (40) is provided on the casing (29) and a discharge duct (36) connected to a vacuum source (not shown) is attached to the lower part of the casing (29). By returning the granular powder (6) sucked by the discharge duct (36) back to the granular powder feeding hopper (11), the granular powder (6) can be reused.

Shape of Open-close Member

Figure 8:
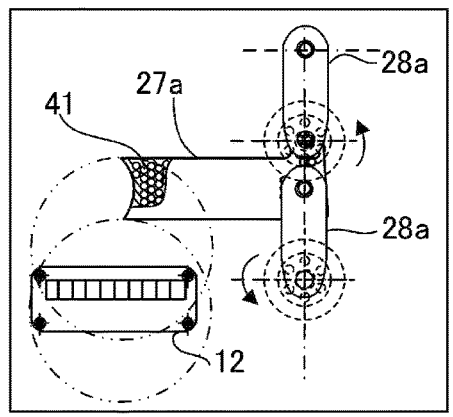
FIG. 8a to FIG. 8f are explanatory drawings for a link mechanism of an open-close member according to Embodiment 2 of the present invention.
Figure 8:
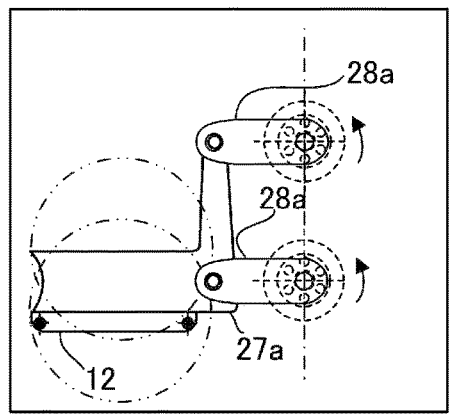
Figure 8:
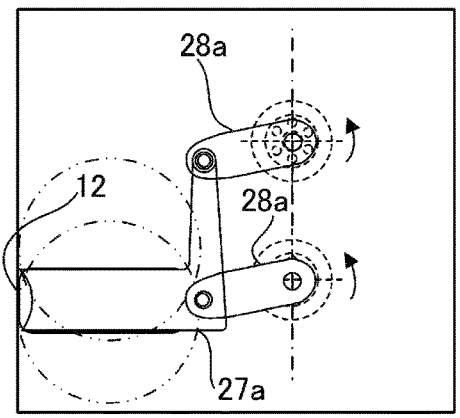
Figure 8:
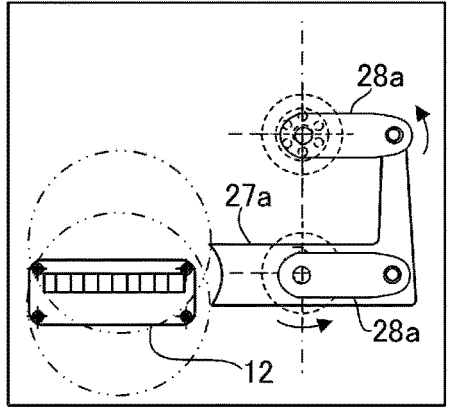
Figure 8:
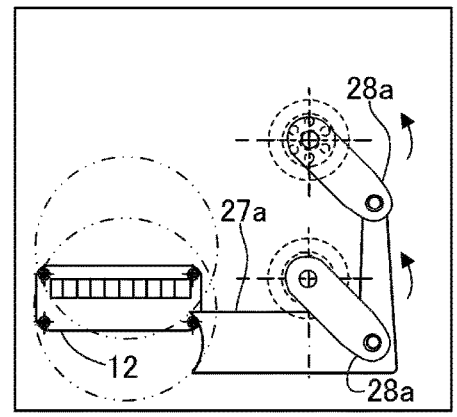
Figure 8:
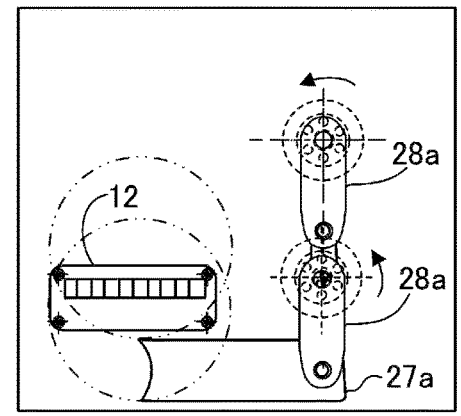
Figure 9:
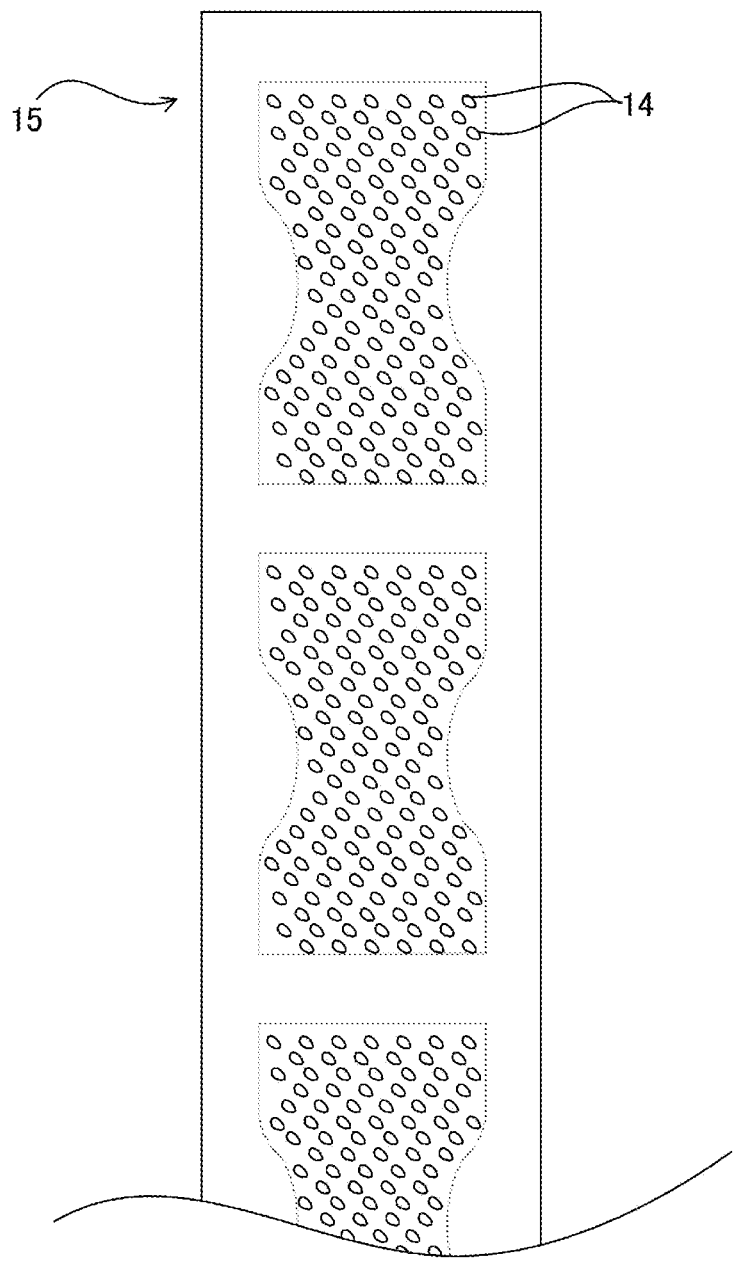
FIG. 9 is a top view showing an example of a granular powder-containing sheet according to Embodiment 2 of the present invention.

The open-close member (27) of Embodiment 1 is, as shown in FIG. 5, plate-like and generally I-shaped in plan view, whereas the open-close member (27b) of Embodiment 2 is, as shown in FIG. 8, nearly L-shaped in plan view. As shown in FIG. 8, two positions of the near L-shaped open-close member (27a) are rotationally driven via link arms (28a) respectively, and with a quadruple link thus formed, the near L-shaped open-close member (27a) is kept parallel and is unidirectionally rotated. The near L-shaped open-close member (27a) is driven in a direction orthogonal to the width direction of the first sheet material (4) so as to diagonally intersect the feeding passage (12) of the granular powder (6) from an upper part of one side of the feeding passage (12) to a lower part of the other side by a repeated motion of FIG. 8a→FIG. 8b→FIG. 8c→FIG. 8d→FIG. 8e→FIG. 8e→FIG. 8f, that opens and closes the feeding passage (12). Also, in pursuit of high speed operation, the open-close member (27a) employs a honeycombed structure having a large number of hollows (41) therein for weight reduction without impairment of its strength. In this embodiment, a single piece of the open-close member (27a) is rotated, but the configuration is not limited thereto, and for example, in another embodiment, a plurality of pieces of the open-close member (27a) may be used and alternately rotated for opening and closing the feeding passage (12) at a higher speed.

Use of a Plurality of Open-close Members

An intermittent feeding of the granular powder (6) can be achieved by an open-close member that intersects the feeding passage (12) of the granular powder (6) and thereby opens and closes the feeding passage, but in such a case where the production apparatus is to be stopped or rested and attempt is made to halt the feeding of the granular powder (6), an immediate closing of the feeding passage (12) by a rotationally driven open-close member is difficult because it is required to quickly stop the open-close member rotating at a high speed, at the closing position. To solve this problem, as shown in FIG. 6 and FIG. 7, is employed a configuration in which a second open-close member (38) is provided apart from the first open-close member (27a). During the normal operation of the production apparatus, the feeding passage (12) is opened and closed repeatedly by the first open-close member (27a) so as to intermittently feed the granular powder (6) whereas in the case where the production apparatus is to be stopped or rested, the feeding passage is closed immediately and continuously by the second open-close member (38). Thus, stopping and starting the feeding of the granular powder (6) can be achieved in a manner suitable for the mode of operation of the production apparatus.

Whereas the first open-close member (27a) is kept parallel and is unidirectionally rotated, as stated above, with a quadruple link mechanism, the second open-close member (38) is coupled to a rod of an air cylinder (not shown) so as to be capable of reciprocating motion in a direction parallel to the plane of the paper and intersecting the feeding passage (12). The second open-close member (38) is retreated to such a position as not to obstruct the flow of the granular powder (6) in the feeding passage (12) while the production apparatus is operated; however, when the feeding of the granular powder (6) is intended to be stopped as in a case where the production apparatus is to be stopped, rested, etc., the rod of the air cylinder can be extended to advance the second open-close member (38) to the position shown by the broken line in FIG. 7, so that the second open-close member (38) thus closes the feeding passage (12) immediately and continuously to stop the feeding of the granular powder.

Speed Control of the Open-close Member

An intermittent feeding of the granular powder (6) can be achieved by an open-close member that intersects the feeding passage (12) of the granular powder (6) and thereby opens and closes the feeding passage. In this case, the open-close member for opening and closing the feeding passage (12) is moved preferably not at a constant speed, but at a decreased or increased rotational speed while the feeding passage (12) is closed as compared to the speed thereof in the state where the feeding passage (12) is open. By such a decrease or increase of the rotational speed, the ratio of the length of a portion to which the granular powder (6) is not fed and the length of a portion to which the granular powder (6) is fed can be freely set as required according to the changes in the rotational speed.

For example, in FIG. 6, with use of a motor provided with an inverter control mechanism or, more preferably, a programmable servomotor, as the electric motor (37) that rotationally drives the open-close member (27a), the ratio of the length of a portion to which the granular powder (6) is not fed and the length of a portion to which the granular powder (6) is fed can be freely set as required by changing the rotational speed of the open-close member (27a) partially within one revolution through a sophisticated control of the electric motor (37).

Ratio of Granular Powder Containing Room Portion

In the case where the feeding passage (12) of the granular powder (6) is divided into a plurality of separate passages of which respective widths are short, it is also possible to exclude the granular powder (6) that is flowing in part of the separate passages to the outside of the feeding passage (12) by an appropriate second excluding means (such as mechanical means, blow means or suction means using an air stream or the like, etc.). As the result, the ratio of the granular powder containing room portion in the granular powder-containing sheet produced by the apparatus for producing the granular powder-containing sheet can be appropriately changed as needed. For example, as shown in FIG. 7, a blow duct (39) as the second excluding means communicably connected to a pressurized air source (not shown) may be attached to either side (at a most lateral position in the width direction) of the feeding passage (12) so that part of the granular powder (6) flowing in the outermost passages in the width direction is intermittently blown off to be excluded to the outside of the feeding passage (12). In this way, it is possible to narrow, partially in the length direction in the granular powder-containing sheet (15), the portion in which the container rooms (14) contain the granular powder (6). Here, the ratio of the granular powder containing room portion can be adjusted to the shape of the human body by changing the degree of blowing off with use of the blow ducts (39).

Feeding Position of the Second Sheet Material

The second sheet material (8) is fed, as shown in FIG. 6 and FIG. 7, at a position that is on the downstream side of the receiving position (17a) in the rotational direction of the anvil roller (2) and is as close as possible to the receiving position (17a). Therefore, in Embodiment 2, there is no vacuum retention member, such as the perforated metallic sheet, between the receiving position (17a) and the feeding position of the second sheet material (8). Since the container rooms having received the granular powder (6) are immediately covered with the second sheet material (8), the granular powder (6) is prevented from being scattered around the apparatus.

Guide Member for the Second Sheet Material

As shown in FIG. 6 and FIG. 7, a guide panel (33) is provided as a second feeding means (9) for guiding the second sheet material (8). The front edge of the guide panel (33) is disposed at a position as close as possible to the receiving position (17a) so that, specifically, the length obtained by subtracting the thickness of the second sheet material from the distance between the receiving position and the feeding position is 5 mm or less, and more preferably 2 mm or less. In Embodiment 1 shown in FIG. 1 and FIG. 3, since the second sheet material (8) is fed onto the circumferential surface of the anvil roller (2) by the second feeding means (9) using the guide roller system, a relatively large installation space is required. In contrast, by employing a guiding method with use of the guide panel (33), the installation space can be reduced, the front edge of the guide panel (33) can be disposed as close as possible to the receiving position, and moreover, the structure of the equipment can be simplified because, without any rotary member such as a roll, there is no need to take into account the failure thereof, etc. Also, since the guide panel (33) is disposed between the second sheet material (8) that is guided to the feeding position and the anvil roller (2), the second sheet material (8) is smoothly fed without being influenced by the reduced pressure on the surface of the anvil roller (2). Additionally, the guide panel (33) is preferably formed of a material having a smooth surface and a good wear resistance, for example, stainless steel or ceramics.

Position of the Guide Panel

As shown in FIG. 6 and FIG. 7, the guide panel (33) is disposed so as to lie along a bottom face of the open-close means (13a). By narrowing the space between the open-close means (13a) and the guide panel (33), the air current caused by the reduced pressure inside the recessed portions (20) on the surface of the anvil roller (2) is reduced and hence a disorderly movement of the granular powder (6) due to the air current is suppressed, leading to smooth flow of the granular powder (6) from the feeding passage (12) to the container rooms (14).

Position of the Shaping Roller

The shaping roller (3) is disposed as close as possible to the receiving position (17a). By shortening the distance between the shaping roller (3) and the receiving position (17a), it is possible to reduce the volume of the space under a reduced pressure in the anvil roller (2), to transport the first sheet material (4), on the circumferential surface of the anvil roller (2), downstream in the rotational direction with the container rooms (14) surely sucked and held in the recessed portions (20), and to reduce the energy cost, leading to low cost operation.

Vacuum Retention Member

The vacuum retention member (25), such as perforated metallic sheet or the like, is disposed outside the first sheet material (4), along the circumferential surface of the anvil roller (2) so as to face an area from the shaping roller (3) to the receiving position (17a). With such a vacuum retention member, the first sheet material (4) can be firmly sucked and held on the surface of the anvil roller (2) due to the reduced pressure inside the recessed portions (20) on the surface of the anvil roller (2).

Evacuating Interiors of the Recessed Portions (20) on the Surface of the Anvil Roller (2)

Inside the anvil roller (2) shown in FIG. 6 and FIG. 7 is formed a suction passage similar to the suction passage (22) shown in FIG. 3. Also, suction ducts (34) and (35) formed on a side face of the anvil roller (2) are communicably connected to a vacuum source (not shown), and interiors of the recessed portions (20) are communicably connected to the vacuum source via the suction passage that is formed inside the anvil roller (2) and via the ducts (34) and (35). By this vacuum source, at least interiors of the recessed portions (20) ranging from the shaping position (16) to the joining position (18) are vacuumed.

While the method and the apparatus for producing a granular powder-containing sheet have been described in the above embodiments, the description is nothing more than illustrative examples giving concrete forms to the technical thought of the present invention. Therefore, the shapes, structures, measurements, materials, production procedures, etc. of respective parts are not limited to those shown in the embodiments, and can be modified in varieties of ways within the scope of claims of the present invention.

For example, in the embodiments, the container rooms are formed in the first sheet material by the protruding portions of the shaping roller and the recessed portions of the anvil roller that mesh with each other at the shaping position provided, on the surface of the shaping roller, at the position facing the anvil roller, but the configuration is not limited thereto. In other embodiments, for example, the container rooms may be formed in the first sheet material by recessed portions provided on the circumferential surface of a second shaping roller disposed so as to face the circumferential surface of the shaping roller and by the protruding portions of the shaping roller, the recessed portions and the protruding portions meshing with each other. In this case, the container rooms formed are transferred onto the circumferential surface of the anvil roller, and thereafter transported along the circumferential surface thereof.

Also, in the above embodiments, an ultrasonic welding device is used as the joining means, but the configuration is not limited thereto. In other embodiments, for example, other joining means, such as a heated roller, or a roller for pressure gluing the sheet materials onto which an adhesive such as hot melt or the like is applied may be used.

Further, in the above embodiments, the feeding passage is disposed vertically and the open-close means as the excluding means is provided in the middle part of the feeding passage in the vertical direction, but the configuration is not limited thereto. In other embodiments, for example, the feeding passage may be provided so as to be slanted with respect to the vertical direction, and the open-close means may be provided at the upper end or the lower end of the feeding passage.

Moreover, in the above embodiments, the first sheet material and the second sheet material are joined to each other on the peripheries of the container rooms. In this case, for the granular powder so as not to exist on the peripheries, an excluding means such as blower or the like may be provided. Needless to say, for the joining of the two sheet materials, the area on the peripheries may be joined entirely or only partially.

INDUSTRIAL APPLICABILITY

The method and an apparatus for producing a granular powder-containing sheet of the present invention allow easy handling of a granular powder in the production of the granular powder-containing sheet containing the granular powder between two sheet materials, and therefore, are useful, in particular in the production of absorbers used for disposable wearable goods, and also in the production of granular powder-containing sheets for other applications.

REFERENCE SIGNS LIST 1, 1a apparatus for producing a granular powder-containing sheet
2 anvil roller
3 shaping roller
4 first sheet material
5 first feeding means
6 granular powder
7 granular powder feeding device
8 second sheet material
9 second feeding means
10 joining means
11 granular powder feeding hopper
12 feeding passage
13, 13a open-close means
14 container room
15 granular powder-containing sheet
16 shaping position
17, 17a receiving position
18 joining position
19 protruding portion
20 recessed portion
21 nip roller
22 suction passage
23 evacuation device
24 baffle plate
25 vacuum retention member
26 outlet of the powder feeding hopper (11)
27, 27a open-close member
28, 28a link arm
29 casing
30 mechanical discharge means
31 discharge passage
32 amount regulating device
33 guide panel
34 suction duct
35 suction duct
36 discharge duct
37 electric motor
38 second open-close member
39 blow duct (second excluding means)
40 air intake port
41 hollow

The invention claimed is:

1. A method for producing a powder-containing sheet containing a powder in separated container rooms formed between two sheet materials, the method comprising:
　forming the container rooms in a first sheet material;
　thereafter, transporting the sheet material on a circumferential surface of an anvil roller;
　during the transporting process, allowing the granular powder fed from a granular powder feeding hopper through a feeding passage to be received in the container rooms;

thereafter, covering the container rooms with a second sheet material; and joining the two sheet materials to each other on the peripheries of the container rooms;

opening and closing the feeding passage with an open-close member to discharge part of the granular powder flowing in the feeding passage to the outside of the feeding passage when the feeding passage is blocked by the open-close member; and thereby intermittently feeding the granular powder from the granular powder feeding hopper onto the sheet material.

2. The method for producing a granular powder-containing sheet of claim 1, wherein a shaping roller having a plurality of protruding portions on its circumferential surface is disposed so as to face the anvil roller so that a plurality of recessed portions provided on the circumferential surface of the anvil roller mesh with the protruding portions;

the first sheet material is fed onto the circumferential surface of the shaping roller; and the container rooms are formed in the first sheet material by the protruding portions and the recessed portions that mesh with each other.

3. The method for producing a granular powder-containing sheet of claim 2, wherein the pressure inside the recessed portions of the anvil roller is reduced so that the first sheet material is transported with the container rooms sucked and held in the recessed portions of the anvil roller, to a position at which the first sheet material and the second sheet material are joined to each other.

4. The method for producing a granular powder-containing sheet of claim 1, wherein a position at which the granular powder is received in the container rooms is provided on the downstream side of the top of the anvil roller in the rotational direction thereof.

5. The method for producing a granular powder-containing sheet of claim 4, wherein the second sheet material is fed to a position that is close to the position at which the granular powder is received in the container rooms and is on the downstream side of the position in the rotational direction of the anvil roller.

6. The method for producing a granular powder-containing sheet of claim 1, wherein the two sheet materials are joined to each other by ultrasonic welding.

7. An apparatus for producing a granular powder-containing sheet containing a granular powder in separated container rooms formed between a first sheet material and a second sheet material, the apparatus comprising:

an anvil roller for transporting a first sheet material on the circumferential surface thereof;

a granular powder feeding hopper for feeding the granular powder continuously;

a feeding passage for guiding the granular powder downward from the granular powder feeding hopper;

a joining device for joining the two sheet materials to each other;

a first feeding member for feeding the first sheet material; and a second feeding member for feeding the second sheet material, wherein a receiving position and a joining position are provided in this order along the circumferential surface of the anvil roller in this order from upstream of the rotational direction thereof;

the first feeding member is provided so as to be capable of feeding the first sheet material to an upstream side of the receiving position;

a lower end of the feeding passage faces, at the receiving position, the container rooms formed in the first sheet material;

the second feeding member is capable of feeding the second sheet material to either the joining position or in between the joining position and the receiving position; and the joining device faces the anvil roller at the joining position;

a discharging device to discharge part of the granular powder flowing in the feeding passage to the outside of the feeding passage when the feeding passage is blocked by the open-close member.

8. The apparatus for producing a granular powder-containing sheet of claim 7, wherein a shaping roller having a plurality of protruding portions on its circumferential surface is disposed so as to face the anvil roller on the upstream side of the receiving position, the anvil roller has, on the circumferential surface thereof, a plurality of recessed portions that mesh with the plurality of protruding portions;

a shaping position is provided on the circumferential surface of the shaping roller; and the first feeding member feeds the first sheet material to the shaping position or an upstream side thereof.

9. The apparatus for producing a granular powder-containing sheet of claim 8, further comprising an evacuation device communicably connected to interiors of the recessed portions via a suction passage inside the anvil roller.

10. The apparatus for producing a granular powder-containing sheet of claim 1, wherein the open-close member opens and closes the feeding passage by intersecting the feeding passage; and the open-close member is configured so as to move almost parallel to a tangential line of the circumferential surface of the anvil roller at the receiving position.

11. The apparatus for producing a granular powder-containing sheet of claim 7, wherein the second feeding member that feeds the second sheet material is a guide panel; the guide panel is disposed close to the anvil roller; and a front edge of the guide panel is disposed close to the receiving position.

12. The apparatus for producing a granular powder-containing sheet of claim 7, wherein the joining device is an ultrasonic welding device.

* * * * *